United States Patent [19]

Fuhrmann et al.

[11] Patent Number: 4,855,458

[45] Date of Patent: Aug. 8, 1989

[54] MANUFACTURE OF PHTHALIC ANHYDRIDE BY GAS PHASE OXIDATION OF A MIXTURE OF O-XYLOL AND NAPHTHALENE

[75] Inventors: Werner Fuhrmann, Haltern; Manfred zur Hausen, Marl; Wilfried Krix, Bottrop, all of Fed. Rep. of Germany

[73] Assignee: Hüls Aktiengesellschaft, Marl, Fed. Rep. of Germany

[21] Appl. No.: 203,932

[22] Filed: Jun. 8, 1988

[30] Foreign Application Priority Data

Jun. 11, 1987 [DE] Fed. Rep. of Germany ..... 37194763

[51] Int. Cl.$^4$ .......................................... C07D 307/89
[52] U.S. Cl. ..................................... 549/248; 549/249
[58] Field of Search ................................ 549/248, 249

[56] References Cited

U.S. PATENT DOCUMENTS 4,077,984  3/1978  Blechschmitt et al. .......... 260/346.4
4,472,587  9/1984  Benedetti et al. .................... 549/248

Primary Examiner—Richard L. Raymond
Attorney, Agent, or Firm—Gilbert L. Wells

[57] ABSTRACT

A process for the manufacture of phthalic anhydride by oxidation in the gas phase of an o-xylol napthalene mixture. By producing a solution of 1 to 80 parts by mass naphthalene in 99 to 20 parts by mass o-xylol at a temperature of 0° to 80° C., storing the solution at that temperature, heating the solution only shortly prior to the reaction to 110° to 180° C., atomizing the heated solution into a hot airflow, passing the heated solution over metal oxide catalysts in the gas phase and collecting phthalic anhydride product, a problem-free manufacture of phthalic anhydride is attained.

10 Claims, No Drawings

MANUFACTURE OF PHTHALIC ANHYDRIDE BY GAS PHASE OXIDATION OF A MIXTURE OF O-XYLOL AND NAPHTHALENE

CROSS-REFERENCE TO A RELATED APPLICATION

Applicants claim priority under 35 USC 119 for application No. P 37 19 476.3 filed June 11, 1987 in West Germany.

BACKGROUND OF THE INVENTION

The field of the invention is the manufacture of phthalic anhydride and the invention is particularly concerned with the manufacture of phthalic anhydride from a mixture of o-xylol and naphthalene in the gas phase.

U.S. Pat. Nos. 4,077,984 and 4,472,587; the disclosures of which are incorporated herein by reference, disclose the state of the art of manufacturing phthalic anhydride by the oxidation of o-xylol and naphthalene in the gas phase.

The oxidation of o-xylol, naphthalene, or mixtures thereof, in the gas phase to form phthalic anhydride is known and referred to many times in the literature. The oxidation of mixtures of o-xylol and naphthalene has also been described. Thus, in accordance with U.S. Pat. No. 4,472,587 the feed of o-xylol is substituted by naphthalene, as the age of the catalyst increases. This does not involve losses of production or quality. It is also known that the oxidation of mixtures of o-xylol and naphthalene produces clearly higher yields of phthalic anhydride than the conversion of the individual hydrocarbons alone as disclosed in J. Appl. Chem. USSR 41 (1968), pages 2 223 and 2 224. Due to this fact and other advantages the mixed oxidation route is a process of particular commercial interest.

Phthalic anhydride is manufactured on a large scale from o-xylol, naphthalene or mixtures thereof. In the gas phase oxidation of o-xylol the preheated hydrocarbon is atomized into hot process air having a temperature of about 170° C., and this mixture of o-xylol and air is subjected to oxidation. On the other hand, the processes for the oxidation of naphthalene employ the so-called evaporator principle. In the case of the evaporator principle a primary flow of air is charged with hydrocarbon by being introduced into hot molten naphthalene at about 140° C. After dilution with a further amount of secondary air this mixture of naphthalene and air is subjected to catalytic oxidation. The two processes accordingly require individually different process lay-outs in a plant, depending on the nature of the raw material as disclosed by H. Suter in Phthalsäureanhydrid und seine Verwendung, Darmstadt 1972, page 51. Accordingly, a plant designed for the oxidation of o-xylol is not suitable for the employment of naphthalene without additional expedients, and vice versa.

Processes are known for the gas phase oxidation of mixtures of o-xylol and naphthalene, wherein the evaporator principle for naphthalene on the one hand and of the injection of o-xylol on the other hand have been preserved. The mixtures of hydrocarbon and air are generated in separate parallel process lines according to the process principles peculiar to each. The lines are then combined and fed jointly to the reactor for catalytic gas phase oxidation. This procedure for mixed oxidation was developed from the process of naphthalene oxidation, supplemented by those apparatus parts which permit an additional atomization of o-xylol.

The flexibility in relation to the raw materials constitutes an important criterion when evaluating a process as disclosed by H. Suter, i.b.i.d., page 62. A process which can convert o-xylol and naphthalene under process conditions which as far as possible are identical and which is reliable in operation remains the declared objective of such process commercial development. The feeding of naphthalene as a mixture with o-xylol whilst dispensing with the evaporator principle complies with this concept also in respect to safety, because the evaporator due to its volume and the amount of products contained therein, is subject to special risks, particularly in the Low Energy Process.

The possibility of injecting atomized naphthalene as in the o-xylol process has been mentioned in the literature such as disclosed by H. Suter, i.b.i.d., page 49. However, no process based on such technology exists to date. This is due to a number of difficulties in conducting the process resulting from the particular chemical and physical properties of naphthalene. The problems arise particularly, in conducting this process whenever the hydrocarbon mixture injected into the hot process air, contains more than 20 parts by mass of naphthalene. With higher naphthalene proportions the mixed oxidation results in he formation of organic deposits in the catalyst bed which in turn after a very short time result in differential pressure rises in the reactor combined with the need to reduce the naphthalene injection or to stop the reaction.

SUMMARY OF THE INVENTION

Having in mind the limitations of the prior art it is an object of the present invention to improve the oxidation process for the manufacture of phthalic anhydride from a mixture of o-xylol and naphthalene in the gas phase on metal oxide catalysts.

This oxidation process is improved by:

(a) producing a solution of 1 to 80 parts by mass of naphthalene and 99 to 20 parts by mass of o-xylol at a temperature of 0° to 80° C.;

(b) storing the solution at a temperature of 0° to 80° C.;

(c) immediately prior to carrying out the oxidation process, heating the stored solution of (b) to a reaction temperature of 110° to 180° C.;

(d) atomizing the heated solution of (c) into a hot air flow of 150° to 200° C.;

(e) passing the atomized mixture over metal oxide catalysts; and (f) collecting the phthalic anhydride product.

The gas phase reactor, catalysts and means for recovery of phthalic anhydride disclosed in U.S. Pat. No. 4,077,984 are useful in the present invention. Description of the Preferred Embodiments In order to produce phthalic anhydride by gas phase oxidation, a solution of naphthalene in o-xylol is employed, according to the present invention, and this solution is preferably stored at temperatures below the solidification point of naphthalene. Periods of residence above 78° C. are for brief duration only. Suitable qualities of naphthalene are preferably distilled naphthalene, more particularly freshly distilled naphthalene and/or crystallized naphthalene, in particular those having a solidification point of 78° to 80° C. Other qualities of naphthalene can also be used.

In the process according to the present invention a solution of naphthalene, preferably of a naphthalene as obtained by crystallization and/or distillation, is made in o-xylol at a temperature of 0° to 80° C., preferably 30° to 70° C., in particular 40° to 60° C. Thereafter the solution of o-xylol in naphthalene is kept at a temperature of 0° to 80° C., preferably at 30° to 70° C., in particular at 40 to 60° C. In this manner solutions of 1 to 80 parts by mass of naphthalene, preferably of 30 to 65 parts by mass, in particular of 40 to 60 parts by mass of naphthalene in 99 to 20 parts by mass, preferably of 70 to 35 parts by mass, in particular of 60 to 40 parts by mass of o-xylol are produced and stored at such temperatures practically indefinitely, preferably up to 10 days. The higher temperatures are selected preferably for the solutions rich in naphthalene and the lower temperatures for the solutions of low naphthalene content. Any insoluble portions which may precipitate during storage are preferably separated off.

The solution of naphthalene in o-xylol is withdrawn from the storage vessel by pumping shortly prior to the reaction, heated to temperatures of 110° to 180° C., the heated solution being atomized into a hot flow of air at 150° to 200° C. and passed over metal oxide catalysts. $TiO_2$-$V_2O_5$-catalysts, in particular doped $TiO_2$-$V_2O_5$-catalysts are preferably employed.

In a special embodiment of the process according to the invention, an o-xylol naphthalene solution of higher concentration, up to 80 parts by mass naphthalene, is produced. This solution, the temperature of which initially amounts to less than 80° C., is pumped out of the storage vessel, heated to temperatures of 110° to 180° C. and diluted with further amounts of hot o-xylol to concentrations of 1 to less than 80 parts by mass of naphthalene before such solution is atomized into the hot process air and passed to the gas phase oxidation. Alternatively, the heating-up to 110° to 180° C. may take place only after mixing with the additional amount of o-xylol.

In a preferred embodiment of the process according to the invention, naphthalene is distilled, the fresh distillate is withdrawn by pumping from the distillate collecting vessel preferably within a residence period of up to 60 minutes, in particular up to 20 minutes, for example 15 to 45 minutes at a temperature of 80° to 120° C. The distillate is mixed with 99 to 20 parts by mass of o-xylol to form a solution comprising 1 to 80 parts by mass of naphthalene. The o-xylol naphthalene solution is heated to 110° to 180° C., the heated solution is atomized into hot process air having a temperature of 150° to 200° C. and passed over metal oxide catalysts.

The process according to the present invention permits the problem-free oxidation of an o-xylol naphthalene mixture by direct atomization of the hydrocarbons into hot process air. Under the mild conditions of this process it has now been possible to overcome the previous problems with this novel process. Surprisingly it is found in addition that the naphthoquinone content in the raw PSA of the mixed oxidation amounts to only 1/10 of the content formed when operating with pure naphthalene.

SPECIFIC EXAMPLES

The following examples serve for further elucidation:

EXAMPLE 1

Naphthalene distillate having a solidification point of 79° C. is taken from a distillate receiver and mixed into cold o-xylol to produce a solution of the hydrocarbons containing 60 parts by mass of naphthalene and having a temperature of 60° C. The o-xylol naphthalene mixture is stored under these conditions for 20 days. Thereafter it is pumped out of the storage vessel, mixed with further amounts of hot o-xylol at 160° C. to result in a mixture containing 50 parts by mass naphthalene which is heated to a temperature of 160° C., the heated solution being atomized into hot process air at 170° C. and passed over a $TiO_2/V_2O_5$ catalyst in a 12 000 tube reactor.

The charge rate amounts to 60 g hydrocarbon per Nm3 air at 3.5 Nm³ (cubic meters at normal conditions) per tube per hour, the salt bath temperature being set to 371° C. The mixed oxidation proceeds smoothly and without problems and without any differential pressure rises being noticeable during the period of the example of e.g. 25 days. Phthalic anhydride product is collected.

EXAMPLE 2

Naphthalene is distilled, the distillate (solidification point 79° C.) being pumped out of the receiving vessel after a residence period of 20 minutes and at a temperature of 100° C. and mixed with a hot flow of oxylol of 165° C. so that a solution of the hydrocarbon is formed comprising 50 parts by mass of naphthalene. This mixture is heated to a temperature of 140° C. and oxidized under the conditions of example 1 on $TiO_2/V_2O_5$ catalysts. The mixed oxidation proceeds smoothly and without problems without differential pressure rises being noticeable. Phthalic anhydride product is collected.

EXAMPLE 3

Naphthalene distillate having a solidification point of 79° C. is stored at a temperature of 100° to 110° C. The residence period under these conditions amounts to 20 days. Thereafter the product is pumped out of the storage vessel, mixed with hot o-xylol of 160° C. to form a hydrocarbon mixture comprising 50 parts by naphthalene, the solution of the hydrocarbons being heated to a temperature of 160° C. The heated solution is atomized as in examples 1 and 2 into hot process air of 170° C. and passed over $TiO_2/V_2O_5$ catalysts of a 12 000 tube reactor.

The charge rate is once again 60 g hydrocarbons per Nm3 air at 3.5 Nm3 per tube and hour, the salt bath temperature being again set at 371° C.

The differential pressure across the catalyst at the beginning of the example amounts to 335 mbar. As the mixed oxidation proceeds it rises gradually and continuously, reaching 352 mbar after 3 days, thereafter rising very rapidly to beyond 400 mbar. A stabilization of the differential pressure is possible only by reducing the naphthalene content in the hydrocarbon mixture to 20 parts by mass. A slight reduction to lower values is possible by complete withdrawal f the naphthalene feed, however, a regeneration of the original differential product takes place only after stopping the reaction. Phthalic anhydride product is collected.

We claim:

1. In a process for the manufacture of phthalic anhydride from a gas phase mixture of o-xylol and naphthalene by oxidation in said gas phase on metal oxide catalysts, the improvement consisting essentially of:
   producing a solution of 1 to 80 parts by mass naphthalene and 99 to 20 parts by mass o-xylol at a temperature of about 0° to 80° C., storing said solution at said temperature and heating only shortly prior to the reaction to temperatures of about 110° to 180°, atomizing said heated solution into a hot air flow of about 150° to 200° C., passing said heated solution in a gas phase over metal oxide catalysts and collecting said phthalic anhydride.

2. The process of claim 1, wherein said solutions are 30 to 65% parts by mass of naphthalene and 70 to 35 by mass of o-xylol.

3. The process of claim 2, wherein said solutions are 40 to 60 parts by mass of naphthalene and 60 to 40 parts by mass of o-xylol.

4. The process of claim 1, wherein said naphthalene is freshly distilled naphthalene.

5. The process of claim 1, wherein said naphthalene is crystallized naphthalene, having a solidifying point of 78° to 80° C.

6. The process of claim 1, wherein said solution has a temperature of 30° to 70°.

7. The process of claim 6, wherein said solution has a temperature 40° to 60° C.

8. The process of claim 1, wherein said heated solution having a concentration, up to 80 parts by mass of naphthalene, is diluted with further amounts of o-xylol down to concentrations of from 1 to less than 80 parts by mass naphthalene, and then atomized into said hot airflow of 150° to 200° C.

9. The process of claim 1, wherein said solution having a concentration of up to 80 parts by mass of naphthalene prior to heating is diluted with further amounts of o-xylol down to concentrations of 1 to less than 80 parts by mass of naphthalene and then atomized into said hot flow of air of 150° to 200° C.

10. The process of claim 1, wherein said naphthalene is freshly distilled hot naphthalene of 80° to 120° C. dissolved in o-xylol, said solution is heated to 110 to 180° C. and subsequently atomized into said hot process air and passed over metal oxide catalyst.

* * * * *